(12) United States Patent
Qian et al.

(10) Patent No.: US 8,257,478 B2
(45) Date of Patent: Sep. 4, 2012

(54) USE OF MARINE FUNGUS ORIGINATED COMPOUNDS AS ANTIFOULING AGENTS

(75) Inventors: Pei-Yuan Qian, Hong Kong (CN); Xiancui Li, Hong Kong (CN); Fuk Ning Kwong, Hong Kong (CN); Lai Hung Yang, Hong Kong (CN); Sergey Vladimirovich Dobretsov, Hong Kong (CN)

(73) Assignee: The Hong Kong University of Science and Technology, Kowloon, Hong Kong (CN)

(*) Notice: Subject to any disclaimer, the term of this patent is extended or adjusted under 35 U.S.C. 154(b) by 1936 days.

(21) Appl. No.: 11/303,610

(22) Filed: Dec. 16, 2005

(65) Prior Publication Data
US 2006/0147410 A1 Jul. 6, 2006

Related U.S. Application Data

(60) Provisional application No. 60/636,092, filed on Dec. 16, 2004.

(51) Int. Cl.
| | |
|---|---|
| C09D 5/14 | (2006.01) |
| A01N 37/18 | (2006.01) |
| A01N 43/16 | (2006.01) |
| A01N 37/00 | (2006.01) |
| A01N 25/32 | (2006.01) |
| A61K 31/34 | (2006.01) |
| A61K 31/205 | (2006.01) |
| A61P 31/00 | (2006.01) |
| A61P 31/10 | (2006.01) |
| C04B 9/02 | (2006.01) |

(52) U.S. Cl. ............ 106/15.05; 106/16; 106/18.32; 106/2; 106/14.05; 106/14.34; 106/14.35; 106/14.37; 514/1.1; 514/2.3; 514/2.4; 514/2.9; 514/3.3; 514/458; 514/468; 514/529; 514/547; 514/554; 514/576; 514/734; 514/741; 424/405; 424/406; 424/484; 424/485; 424/486

(58) Field of Classification Search .............. 514/734, 514/741, 1.1, 2.3, 2.4, 2.9, 3.3, 458, 468, 514/529, 547, 554, 576; 424/405, 406, 484, 424/485, 486
See application file for complete search history.

(56) References Cited

U.S. PATENT DOCUMENTS
4,788,302 A 11/1988 Costlow et al.
(Continued)

FOREIGN PATENT DOCUMENTS
JP 05003792 A * 1/1993
(Continued)

OTHER PUBLICATIONS http://en.wikipedia.org/wiki/Antibacterial; citing 2007, Elsevier online—Dorland's Medical Dictionary; downloaded Dec. 20, 2011.*

(Continued)

*Primary Examiner* — Johann Richter
*Assistant Examiner* — Jane C Osewcki
(74) *Attorney, Agent, or Firm* — Saliswanchik, Lloyd & Eisenschenk

(57) ABSTRACT

Compounds originally isolated from marine fungi are useful as antifouling (antibacterial and/or anti-larval settlement) agents. The compounds are 3-chloro-2,5-dihydroxy benzyl alcohol, cyclo-(Pro-Phe),3-methyl-N-(2-phenylethyl) butanamide, and succinic acid. The compounds are non-toxic or low-toxic. They can be used alone or in combination, as active ingredients for making environment-friendly antifouling formulations/coatings.

9 Claims, 14 Drawing Sheets

U.S. PATENT DOCUMENTS

| | | | |
|---|---|---|---|
| 4,886,664 A | | 12/1989 | Jung et al. |
| 4,929,270 A | * | 5/1990 | Cardellina et al. ............ 504/235 |
| 5,290,693 A | | 3/1994 | Chen et al. |
| 5,607,741 A | | 3/1997 | Zimmerman et al. |
| 5,695,552 A | * | 12/1997 | Taylor ........................ 106/15.05 |
| 5,833,742 A | * | 11/1998 | Willingham et al. ...... 106/18.32 |
| 5,919,689 A | | 7/1999 | Selvig et al. |
| 5,989,323 A | | 11/1999 | Taylor |
| 6,210,947 B1 | | 4/2001 | Dobson |
| 6,342,386 B1 | | 1/2002 | Powers et al. |
| 6,395,866 B1 | * | 5/2002 | Miyamoto et al. ......... 528/295.5 |
| 6,635,692 B1 | * | 10/2003 | Christie et al. ................ 523/122 |
| 2005/0195025 A1 | * | 9/2005 | Leenerts et al. ............... 330/10 |

FOREIGN PATENT DOCUMENTS

| | | | |
|---|---|---|---|
| KR | 2003055089 A | * | 7/2003 |
| WO | 95/27009 A1 | | 11/1995 |

OTHER PUBLICATIONS http://en.wikipedia.org/wiki/Biofouling; citing referenced materials from "Marine Fouling and Its Prevention", (1952) U.S. Naval Institute, Annapolis, MD; "Progress in Organic Coatings" (Jul. 2004), 50(2): 75-104; and "Marine Pollution Bulletin" (Jan. 1995), 30(1): 14-21; downloaded Dec. 20, 2011.*

* cited by examiner

USE OF MARINE FUNGUS ORIGINATED COMPOUNDS AS ANTIFOULING AGENTS

CROSS REFERENCE TO RELATED APPLICATION

This application claims priority under 35 U.S.C. §119(e) to U.S. Provisional Application Ser. No. 60/636,092, filed Dec. 16, 2004, the disclosure of which is incorporated by reference herein in its entirety.

FIELD OF THE INVENTION

The present invention relates to antifouling compounds originated from marine fungi and to their practical uses in industries. Particularly, the invention relates to antifouling compounds isolated from *Ampelomyces* sp., *Fusarium* sp. and a marine fungus associated with *Acanthella cavernosa*. The compounds possess both antibacterial and anti-larval settlement activities, whereby producing significant and useful antifouling effects.

BACKGROUND OF THE INVENTION

Industrial facilities operating in the marine environment, such as water pipes, power plant water intake systems, sewer pipes, boat hulls, propellers, heat exchangers, grids, fish nets, cages, etc, are prone to marine biofouling. Marine microorganisms such as bacteria, algae, fungi, and protozoa attach to the exposed marine surface and establish colonies, which result in the formation of a slime layer (referring as biofilm). The development of biofilm can also refer to microfouling that not only serves as a source of chemical cues for settlement of invertebrate larvae and algal spores—leading to establishment of macrofouler communities (macrofouling), but also secretes harmful chemicals to building materials of ship hull (corrosion). Macrofoulers such as mussels, tubeworms and barnacles with a calcareous shell or tubes are particularly troublesome as they frequently clog pipes or become attached to submerged surfaces and thus interfere with normal maritime operations.

Biofouling (both microfouling and macrofouling) of underwater structures results in significant economic losses to industry. Decreased fuel efficiency, increased cleaning and maintenance expenses, as well as outage expenses all contribute to increased economic expenditures. Marine bacteria and marine invertebrates such as *Hydroides elegans* and *Balanus amphitrite* are the main factors causing biofouling and biocorrosion. Fouling and biocorrosion are interrelated phenomena and cause significant problems and expense to the shipping industry and mariculture. Biofouling can increase the frictional force on a ship's hull by at least 10%, decrease the power of the propellers by 20%, and require over 50% more fuel to maintain a ship at a desired speed. Furthermore, biofouling can accelerate ship hull corrosion by 200% and shorten the life-time of ship hulls by 50%. Economic and environmental losses due to biofouling have amounted up to several billion US dollars annually. Production of toxic antifouling coatings as well as disposal of the spent coatings has caused another several billions of US dollars per year. Over the last 30 years, TBT-based antifouling coating has been the most effective antifouling paints, however, due to its highly toxic nature and considerable and persistent stress on the marine environment, production of TBT-based marine coating has been banned in 1 Jan. 2003 (IMO, 2003). There is an urgent need to find new environment friendly antifouling compounds.

Microorganisms are a sustainable biological source, which may provide new clues for solutions to the problems we are facing today. The use of microorganisms has advantages in reproducible production on a large scale as compared with the use of higher animals or plants. In addition, the microbial fermentations are economically favorable due to low manpower requirements for operation of the fermentation process. Of course, once suitable chemicals originated in marine microorganisms are identified for their antibiotic and antifouling effects, those compounds may be more economically produced by chemical synthesis on an industrial scale.

SUMMARY OF THE INVENTION

Four chemical compounds originated in marine fungi are identified for their possessing significant antifouling (through both antibacterial and anti-larval settlement) effects and their being non-toxic or low-toxic to marine animals. The compounds are the following:

(i) 3-chloro-2,5-dihydroxy benzyl alcohol (Compound 1)

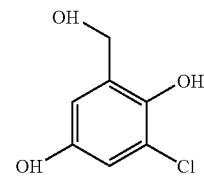

(ii) cyclo-(Pro-Phe) (Compound 2)

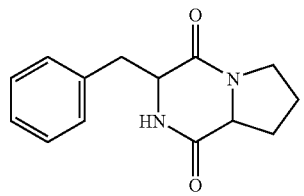

(iii) 3-methyl-N-(2-phenylethyl) butanamide (Compound 3)

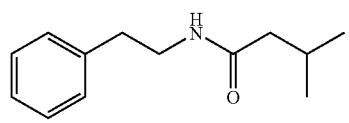

(iv) succinic acid (Compound 4)

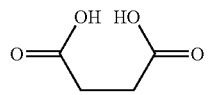

It is contemplated that various substitutions on the base compounds listed above may be made by people with ordinary skill in the art to produce satisfactory antifouling (antibacterial and anti-larval settlement) effects. For example, —Cl in compound 2 may be replaced with —F.

It is an object of the present invention to provide an environment-friendly method for preventing fouling organisms from settling on submarine surfaces by using an antifouling formulation containing one or more of the above listed compounds or their functional derivatives.

As another aspect of the invention, there is provided a method for developing a marine paint that is non-toxic, non-heavy-metal-based and benign to the marine environment by using one or more of the above listed compounds or their functional derivatives.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF THE INVENTION

Figure 1:
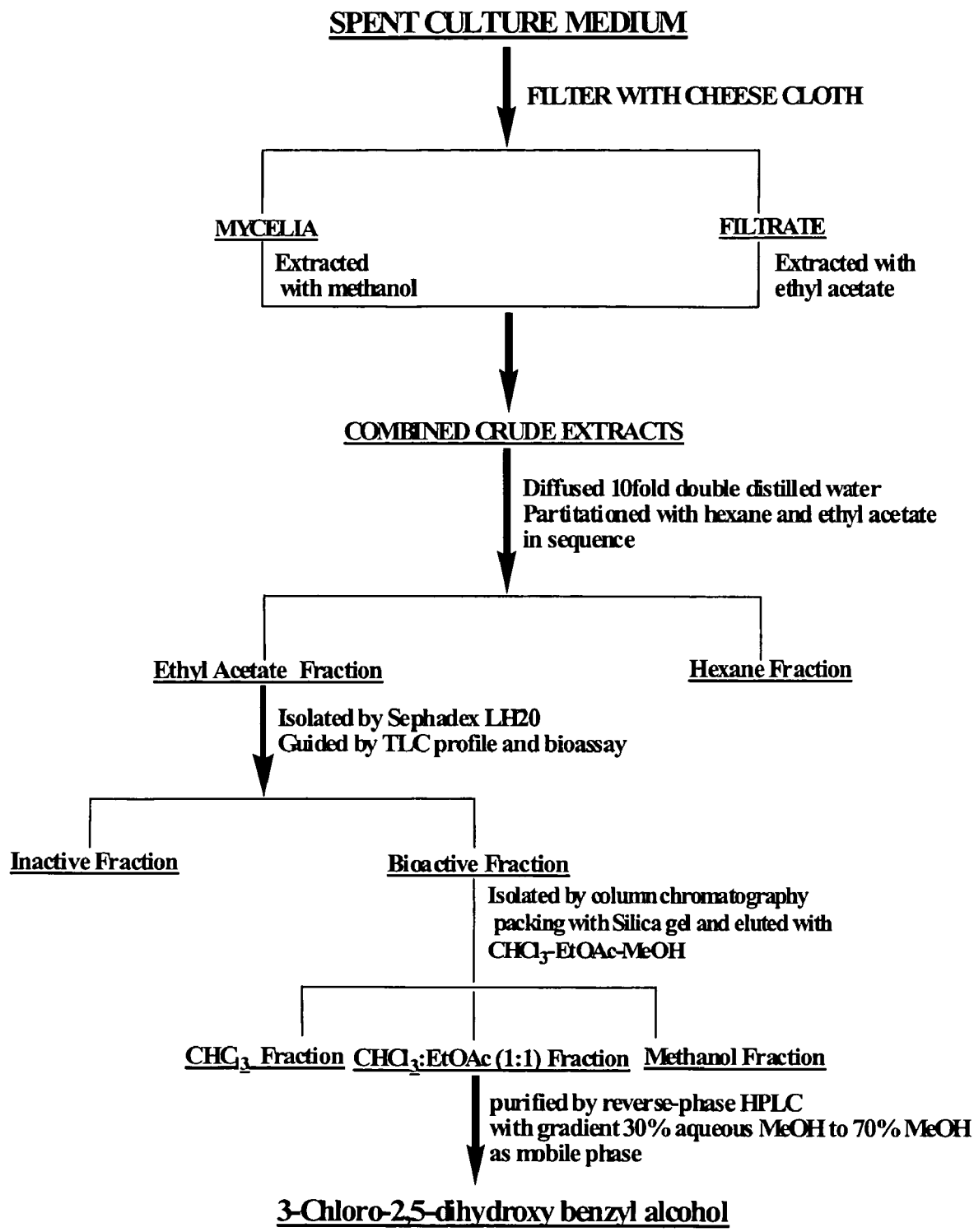
FIG. 1 outlines the procedure used for producing 3-chloro-2,5-dihydroxybenzyl alcohol from *Ampelomyces* sp.

A. Marine Fungi Strains Use in Producing Antibacterial and Antifouling Compounds UST040128-009, a fungus strain identified as an *Ampelomyces* sp., was isolated from the 6-day-old natural biofilm developed on a glass slide in Hong Kong marine waters in January 2004. The biofilm on the glass was scrapped off by using a sterile cover slip and was then suspended in 500 µl of sterile Ringer solution (Oxoid). The sample was diluted 10 and 100 fold with autoclaved Ringer solution. Aliquots of 200 µl from the suspension was spread on corn meal agar (CMA, Oxoid) plate with 0.3% Rose Bengal (Acros) to inhibit fast-growing fungi. The antibiotics (streptomycin (USB) and penicillin G (Sigma)) at final concentrations of 100 mg L$^{-1}$ were also added to the agar plate to inhibit the growth of bacteria. The inoculated agar plate was incubated at 25° C. and examined daily under a dissection microscope for the presence of developing fungal hyphae beginning from two days after inoculation. Distinct fungal colonies on the agar plates were transferred to new CMA plates for isolation and purification. *Ampelomyces* sp. was identified by its DNA sequence in ITS2 rRNA region (see SEQ ID No:1).

UST030110-009, a strain of fungus associated with marine sponge *Acanthella cavernosa*, was isolated from the sponge tissues that were collected by SCUBA (Self-contained Underwater Breathing Apparatus) from a shallow water reef at Sanya Bay, Hainan Island, P. R. China. Each specimen was carefully dislodged from the reef and placed in a clean plastic bag, brought to the water surface by a diver, kept in a cooler, and brought to the nearby Sanya Joint Laboratory of Marine Science (HKUST-CAS). The specimen was cut into pieces using a sterile knife and was then suspended in 500 µl of sterile Ringer solution (Oxoid). The sample was diluted 10 and 100 fold with autoclaved Ringer solution. Aliquots of 200 µl from the suspension was spread on corn meal agar (CMA, Oxoid) plated with 0.3% Rose Bengal (Acros) to inhibit fast-growing fungi. The antibiotics (streptomycin (USB) and penicillin G (Sigma)) at final concentrations of 100 mg L$^{-1}$ were also added to the agar plate to inhibit bacterial growth. The inoculated agar plate was incubated at 25° C. and examined daily under a dissection microscope for the presence of developing fungal hyphae beginning from two days after inoculation. Distinct fungal colonies on the agar plates were transferred to new CMA plates for isolation and purification. This fungus strain was identified by its DNA sequences in 18S rRNA region and ITS region (see SEQ ID No: 4 and SEQ ID No: 5, respectively).

*Fusarium* sp. is a marine fungus identified by its DNA sequence in the 18S rRNA (see SEQ ID No: 2) and ITS region (see SEQ ID No: 3).

B. Antifouling Chemical Compounds Produced by Marine Fungi (1) 3-chloro-2,5-dihydroxy benzyl alcohol The *Ampelomyces* sp. strain was grown in liquid culture in 6 replicate 2.8 L flasks each containing 2 L of a seawater-based GYP medium (comprising 2.0% glucose, 0.5% yeast extract, and 0.5% mycological peptone). The cultures were incubated for 21 days on an orbital shaker at 80 rpm at room temperature (about 24° C.).

The actively growing edges of a stock culture colony were used to inoculate 2.8 L Erlenmeyer flasks containing 2 L of sterile culture medium, containing glucose (20 g $L^{-1}$), peptone (10 g $L^{-1}$), sea water (800 ml $L^{-1}$) and fresh water (200 ml $L^{-1}$). The cultures were grown for 21 days on a reciprocating shaker at 80 rpm. Antibacterial activity was observed in extraction of both the mycelia and in the cell-free liquid portion of the fermentation culture. Thus, in order to efficiently extract the antibacterial compounds, it was desirable to separate the mycelia from the broth by filtration through cheese cloth.

FIG. 1 outlines the procedures used for extracting and purifying the active compound from a fungal culture. Following the fermentation, the mycelium and broth were separated by filtration through cheese cloth. The cell-free filtrate was extracted with ethyl acetate thrice (filtrate:ethyl acetate 3:1 by volume). Ethyl acetate extract was then combined and concentrated in vacuo (Other suitable solvents such as ethyl acetate, methylene chloride, chloroform, diethyl ether and butanol can also be used for the extraction of the antibacterial compounds from the cultures). The mycelia were extracted with methanol thrice (Other suitable solvents such as ethanol, butanol, acetone and ethyl acetate can also be used here). For an efficient extraction it was desirable to use ultrasonic or a mortar and pestle and clean sand to ground the cells. The methanol extract was concentrated under reduced pressure.

The ethyl acetate and methanol crude extracts (3.78 g, brown in color) were combined. The crude extract was suspended in 10-fold volume of double distilled water, and partitioned with hexane and ethyl acetate subsequently with equal volume of solvents. Other suitable chemical agents may also be used satisfactorily in this step. For example, petroleum ether can replace hexane and diethyl ether, and chloroform or butanol can replace ethyl acetate.

The ethyl acetate residue was passed through Sephadex LH-20, using MeOH as the eluent at the flow rate of 1 ml/min. Fractions of 4 ml $tube^{-1}$ were collected and combined on the basis of TLC [Si gel, $CHCl_3$-MeOH 5:1]. The combined fractions were then tested with antifouling (antibacterial and anti-larval settlement) assays. Fractions containing the active compound were combined and further purified, using silica gel column chromatography (230-400 mesh, E. Merck) column (1.0×50 cm) with a $CHCl_3$-EtOAc-MeOH gradient as the eluent. The active fraction was eluted by dichloromethane-ethyl acetate (1:1) and then purified by reverse-phase HPLC, (Lichrospher 100 RP $C_{18}$ EC 5μ, 250×4 mm i.d.; gradient 30% aqueous MeOH to 70% MeOH) with Waters 600 pump, monitored by Waters 2487 Dual λ Absorbance Detector. The flow rate of the HPLC was kept at 1 ml $min^{-1}$ in order to afford a pure compound that was soluble at 25° C. in methanol, ethanol, propanol, butanol, ethyl acetate, acetone and acetonitrile and, as detailed below, was identified as 3-chloro-2,5-dihydroxy benzyl alcohol.

The structure of this compound was determined by using NMR ($^1$HNMR, $^{13}$CNMR, DEPT and COSY) and the molecular weight was determined by electrospray ionization-mass spectroscopy, which was performed on a Waters Micromass ZQ equipped with an electrospray source. The electrospray source was switched to negative ion mode to acquire negative ion spectra. During the data acquisition, the mass spectrometer probe voltage was maintained at 2.5 kV; the cone voltage was maintained at 18 V and the extractor voltage was 2 V; the source temperature was kept at 100° C. and the desolvation temperature 300° C.; and the drying gas flow rate was 200 L $hr^{-1}$. The 3-chloro-2,5-dihydroxy benzyl alcohol was dissolved in MeOH—$H_2O$-formic acid (90:9.5:0.5) and was injected into the carrier gas stream of the electrospray source at a flow rate of 5 μL $min^{-1}$ through a Hamilton 250 L syringe by using a syringe pump.

The mass spectrum of 3-chloro-2,5-dihydroxy benzyl alcohol showed a molecular ion ([M-H]) at m/z: 172.8 (100.0%), 174.7 (32.6%). Mass spectrum showed that the intensity of (M-H)+2 was ⅓ of that of [M-H], meaning that the compound contains one chlorine.

Proton nuclear magnetic resonance spectra of 3-chloro-2,5-dihydroxy benzyl alcohol in $CD_3OD$ were obtained on a JEOL Model JNM EX-400 at 400 MHz. The data are presented in Table 1.

TABLE 1

$^1$HNMR Spectra of 3-chloro-2,5-dihydroxy benzyl alcohol

| # of Protons | Chemical Shift (δ) (ppm) | Pattern |
|---|---|---|
| 4 | 6.63 | 1H, d |
| 6 | 6.69 | 1H, d |
| 7 | 4.58 | 2H, s |

Carbon-13 nuclear magnetic resonance spectra of 3-chloro-2,5-dihydroxy benzyl alcohol in $CDCl_3$ were obtained on a JEOL Model JNM EX-400 at 100 MHz. The data are presented in Table 2.

TABLE 2

$^{13}$CNMR Spectra of 3-chloro-2,5-dihydroxy benzyl alcohol

| Chemical Shift (δ) (ppm) | Pattern | Assignment |
|---|---|---|
| 61.13 | $CH_2$ | 7 |
| 114.46 | CH | 6 |
| 115.38 | CH | 4 |
| 121.84 | C | 3 |
| 132.04 | C | 1 |
| 144.25 | C | 2 |
| 151.70 | C | 5 |

(2) Cyclo(D)-Pro-(D)-Phe and 3-methyl-N-(2-phenylethyl)butanamide

Figure 2:
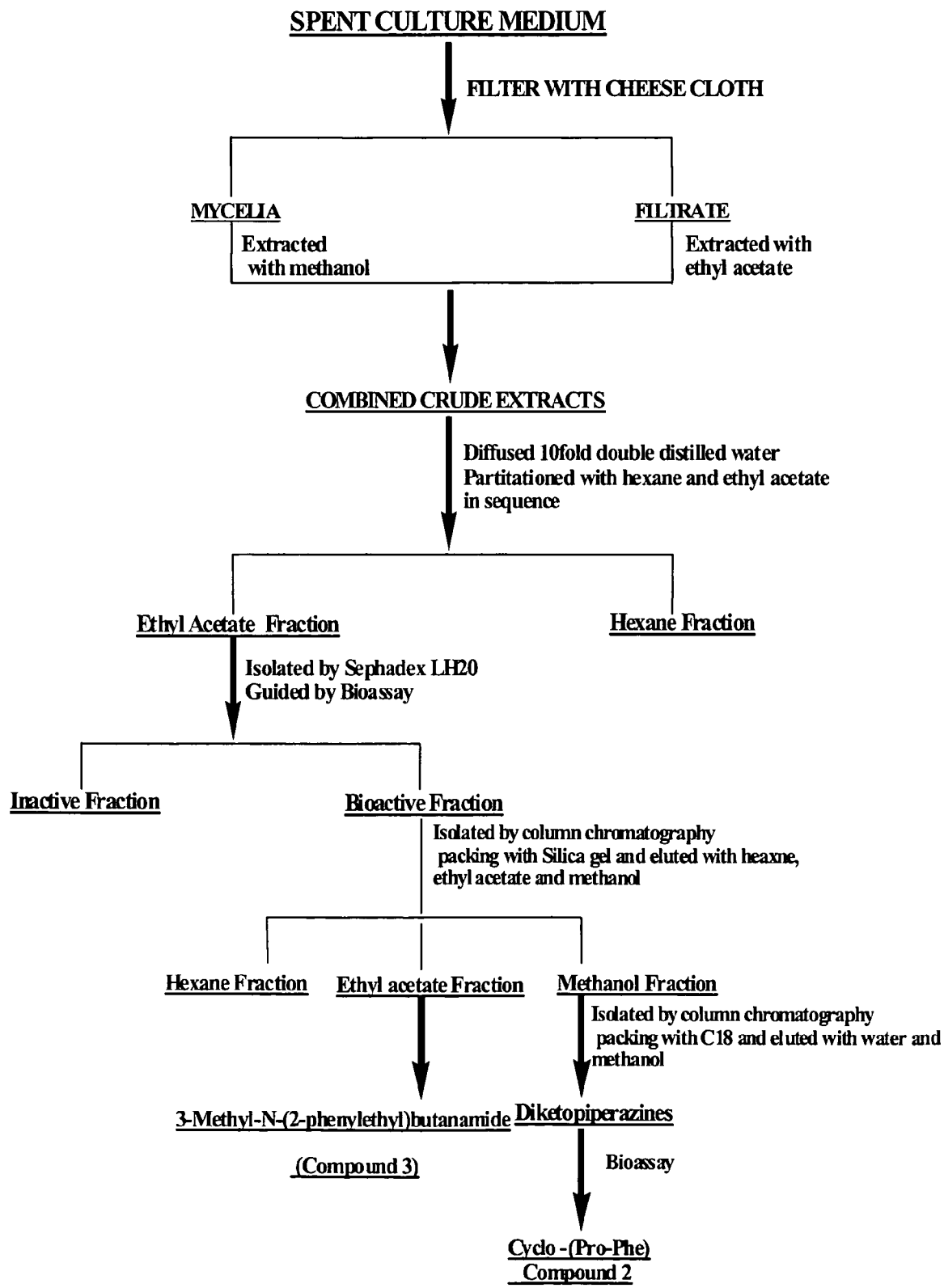
FIG. 2 outlines the procedure used for producing cyclo-(Phe-Pro) and 3-methyl-N-(2-phenylethyl) butanamide from UST030110-009.

FIG. 2 outlines the procedure for production and purification of chemical compounds cyclo(D)-Pro-(D)-Phe and 3-methyl-N-(2-phenylethyl)butanamide from UST030110-009. The actively growing edges of a stock culture colony were used to inoculate 3 L Erlenmeyer flasks containing 1.5 L of sterile culture medium, containing glucose (20 g $L^{-1}$), peptone (10 g $L^{-1}$), sea water (800 ml $L^{-1}$) and fresh water (200 ml $L^{-1}$). The cultures were grown for 15 days on a reciprocating shaker at 120 rpm. Antibacterial activity was observed in extraction of both the mycelia and in the cell-free liquid portion of the fermentation culture. Thus, in order to efficiently extract the antibacterial compounds, it was desirable to separate the mycelia from the broth by filtration through cheese cloth.

For extracting and purifying the bioactive chemical compounds, the cell-free filtrate was extracted with ethyl acetate thrice (filtrate:ethyl acetate 3:1 by volume). The ethyl acetate extract was then combined and concentrated in vacuo (Other suitable solvents such as ethyl acetate, methylene chloride, chloroform, diethyl ether and butanol may also be used for extraction of the antibiotics from the cultures). The mycelia were extracted with methanol thrice. (Again, other suitable solvents such as ethanol, butanol, acetone and ethyl acetate may also be used here). For an efficient extraction it was desirable to use ultrasonic or a mortar and pestle and clean sand to grind the cells. The methanol extract was concentrated under reduced pressure.

The ethyl acetate and methanol crude extracts were combined. The crude extract was suspended in 10-fold volume of double distilled water and partitioned with hexane and ethyl acetate subsequently with equal volume of solvents. Other suitable chemical agents may also be used satisfactorily in this step. For example, petroleum ether can replace hexane and diethyl ether, and chloroform or butanol can replace ethyl ether.

The ethyl acetate extract was loaded on Sephadex LH-20 column and eluted with methanol at the flow rate of 1 ml $min^{-1}$. The fraction size was 5 ml $tube^{-1}$. After running disc diffusion bioassay, the bioactive fractions were pooled and concentrated under reduced pressure. The further purification was performed by using silica gel column chromatography eluted with hexane-ethyl acetate (from 100% hexane to 100% ethyl acetate) and ethyl acetate-methanol (from 100% ethyl acetate to 100% methanol).

The ethyl acetate fraction formed crystals after ethyl acetate evaporated slowly. The purity of crystal was checked on reverse-phase HPLC (Lichrospher 100 RP $C_{18}$ EC 5μ, 250×4 mm i.d.; gradient 50% aqueous $CH_3CN$ to 80% $CH_3CN$) with Waters 600 pump and controller with Waters 717 autosampler, monitored by Waters 996 Photo Diode Array Detector. The HPLC flow rate was 1 ml $min^{-1}$. In the resultant chromatogram, only one major single peak appeared, indicating that the crystal was a pure compound (Compound 2).

The methanol fraction was loaded on an ODS column eluted with $H_2O$-methanol. Each fraction was 3 ml $tube^{-1}$. After analyzing the purity and bioactivity of each fraction, one pure compound was obtained (Compound 3).

The structures of the two compounds were analyzed by NMR ($^1$HNMR, $^{13}$CNMR, DEPT and COSY). Compound 2 was subsequently identified as cyclo-(D)-Pro-(D)-Phe and appeared as white powder. This compound was soluble at 25° C. in methanol, ethanol, propanol, butanol, ethyl acetate acetone and acetonitrile. Determination of its molecular weight was carried out on a Waters Micromass ZQ equipped with an electrospray source that was switched to positive ion mode to acquire positive ion spectra. During the data acquisition, the mass spectrometer probe voltage was maintained at 2.5 kV; the cone voltage was maintained at 18 V and the extractor voltage 2 V; the source temperature was kept at 100° C. the desolvation temperature was set at 300° C.; and the drying gas flow rate was 200 L $h^{-1}$. The cyclo-(D)-Pro-(D)-Phe was dissolved in MeOH—$H_2O$-formic acid (90:9.5:0.5) and was injected into the carrier gas stream of the electrospray source at a flow rate of 5 μL $min^{-1}$ through a Hamilton 250 μL syringe by using a syringe pump. The mass spectrum of cyclo-(D)-Pro-(D)-Phe showed a molecular ion at m/z: 244.9 (100.0%), 245.9 (15.9%).

Proton nuclear magnetic resonance spectra of cyclo (D)-Pro-(D)-Phe in $CD_3OD$ were obtained a JEOL Model JNM EX-400 at 400 MHz. The data are presented in Table 3.

TABLE 3

$^1$HNMR Spectra of cyclo (D)-Pro-(D)-Phe

| # of Protons | Chemical Shift (δ) (ppm) | |
|---|---|---|
| 3 | 3.29-3.37 | 1H, m |
|   | 3.47-3.55 | 1H, m |
| 4 | 1.74-1.81 | 2H, m |
| 5 | 2.00-2.10 | 1H, m |
|   | 1.17-1.25 | 1H, m |
| 6 | 4.01-4.06 | 1H, m |
| N—H | 4.57 | 1H, brs |
| 9 | 4.42 | 1H, d |
| 10 | 3.13 | 2H, d |
| Ar | 7.27-7.18 | 5H, m |

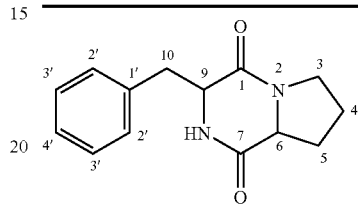

Carbon-13 nuclear magnetic resonance spectra of cyclo (D)-Pro-(D)-Phe in $CD_3OD$ were obtained on a JEOL Model JNM EX-400 at 100 MHz. The data are presented in Table 4.

TABLE 4

$^{13}$CNMR Spectra of cyclo (D)-Pro-(D)-Phe

| Chemical Shift (δ) (ppm) | Pattern | Assignment |
|---|---|---|
| 22.60 | $CH_2$ | 4 |
| 29.19 | $CH_2$ | 5 |
| 37.99 | $CH_2$ | 10 |
| 45.75 | $CH_2$ | 3 |
| 57.45 | CH | 9 |
| 59.82 | CH | 6 |
| 127.69 | CH | 4' |
| 129.06 | CH | 3' |
| 130.65 | CH | 2' |
| 136.95 | C | 1' |
| 166.44 | C | 7 |
| 170.46 | C | 1 |

Compound 3 was subsequently identified as 3-methyl-N-(2-phenylethyl) butanamide and appeared as a colorless crystal. This compound was soluble at 25° C. in methanol, ethanol, propanol, butanol, ethyl acetate acetone, chloroform, dichloromethane and acetonitrile. The molecular weight of this compound was determined on ESI-MS in positive mode. It was dissolved in MeOH—$H_2O$-formic acid (90:9.5:0.5) and was injected into the carrier gas stream of the electrospray source at a flow rate of 5 μL $min^{-1}$ through a Hamilton 250 μL syringe using a syringe pump. The mass spectrum of butanamide showed a molecular ion at m/z: 205.8.

Proton nuclear magnetic resonance spectra of butanamide in $CDCl_3$ were obtained on a JEOL Model JNM EX-400 at 400 MHz. The data are presented in Table 5.

TABLE 5

$^1$HNMR Spectra of 3-methyl-N-(2-phenylethyl) butanamide

| # of Protons | Chemical Shift (δ) (ppm) | |
|---|---|---|
| 1' | 3.41 | 2H, q |
| 2' | 2.70 | 2H, t |

TABLE 5-continued

<sup>1</sup>HNMR Spectra of 3-methyl-N-(2-phenylethyl) butanamide

| # of Protons | Chemical Shift (δ) (ppm) | |
|---|---|---|
| 3 | 1.94 | 1H, m |
| 2 | 1.86 | 2H, d |
| 1 | 0.80 | 6H, m |
| N—H | 5.30 | 1H, brs |
| Ar | 7.20-7.06 | 5H, m |

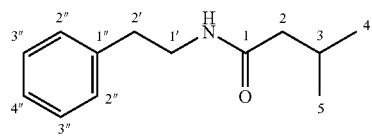

Carbon-13 nuclear magnetic resonance spectra of butanamide in CDCl$_3$ were obtained on a JEOL Model JNM EX-400 at 100 MHz. The data presented in Table 6.

TABLE 6

<sup>13</sup>C NMR Spectra of butanamide

| Chemical Shift (δ) (ppm) | Pattern | Assignment |
|---|---|---|
| 22.40 | CH$_3$ | 4, 5 |
| 26.07 | CH | 3 |
| 35.73 | CH$_2$ | 2' |
| 40.35 | CH$_2$ | 1' |
| 46.12 | CH | 2 |
| 126.26 | CH | 4" |
| 128.38 | CH | 2'" |
| 128.51 | CH | 3" |
| 138.65 | C | 1'" |
| 172.09 | C | 1 |

(3) Succinic Acid

The actively growing edges of a *Fusarium* sp. stock culture colony were used to inoculate 3 L Erlenmeyer flasks containing 1.5 L of sterile culture medium, which contained glucose (20 g L$^{-1}$), peptone (10 g L$^{-1}$), sea water (800 ml L$^{-1}$) and fresh water (200 ml L$^{-1}$). The cultures were grown for 10 days on a reciprocating shaker at 120 rpm. Antifouling (antibacterial and anti-larval settlement) activity was observed in the extracts of both the mycelia and in the cell-free liquid portion of the fermentation culture. Thus, in order to efficiently extract the succinic acid, it was desirable to separate the mycelia from the broth by filtration through cheese cloth, following by washing with autoclaved ddH$_2$O.

Figure 3:
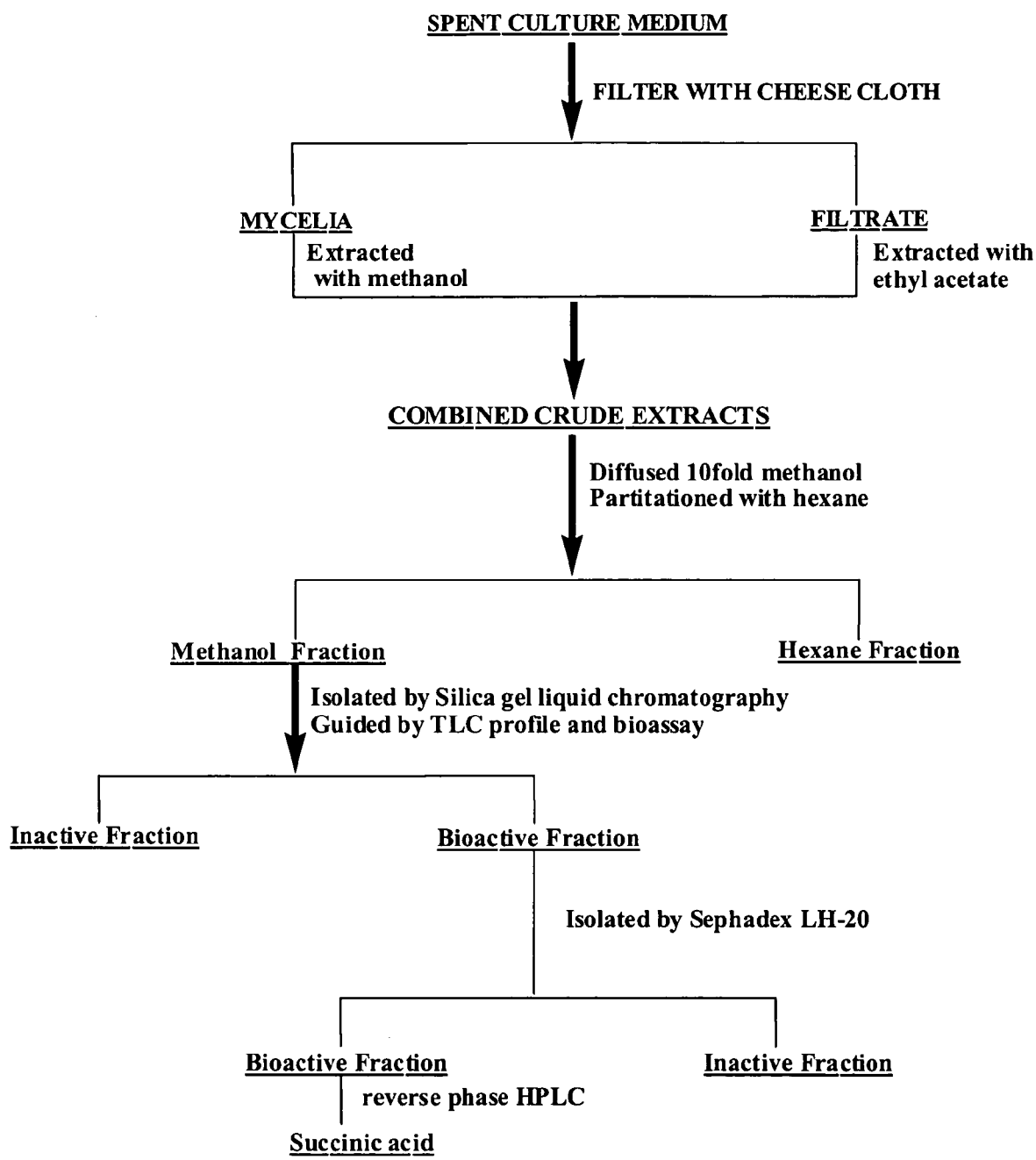
FIG. 3 outlines the procedure used for producing succinic acid from *Fusarium* sp.

FIG. 3 outlines the procedures used for extracting and purifying succinic acid. The cell-free filtrate was extracted with ethyl acetate thrice (filtrate:ethyl acetate 3:1 by volume). The ethyl acetate extract was then combined and concentrated in vacuo (Other suitable solvents such as methylene chloride, chloroform, diethyl ether and butanol may also be used for extraction of the antibiotics from the cultures). The mycelia were extracted with methanol thrice (Again, other suitable solvents such as ethanol, butanol, acetone and ethyl acetate may also be used). For an efficient extraction it was desirable to use ultrasonic or a mortar and pestle and clean sand to ground the cells. The methanol extract was concentrated under reduced pressure.

The ethyl acetate and methanol crude extracts were combined and dried in vacuo at 35° C. Around 1.6 g of organic extract was obtained. The crude extract was suspended in 10 ml methanol and partitioned with hexane and resulted in one gram of bioactive methanol-extract (Petroleum ether can replace hexane). The MeOH extract was subjected to silica gel liquid chromatography using a step-wise gradient profile from 100% DCM to 100% MeOH to yield 9 fractions. The fraction (600 mg) with 15% dichloromethane showed antibacterial activity. The bioactive fraction was further separated by using Sephadex LH-20 and resulted in 30 fractions. Four out of the 30 fractions showed antibacterial activity. The active fractions were combined and further purified by using reversed phase HPLC (Lichrospher 100 RP C$_{18}$ EC 5µ, 250×4 mm i.d.; gradient 90% aqueous CH$_3$CN to 10% CH$_3$CN) at the flow rate of 1 ml min$^{-1}$.

The structure was elucidated through $^1$H NMR, $^{13}$C NMR, X-ray diffraction and further confirmed by mass spectroscopy. The active compound was identified as succinic acid. The molecular weight of succinic acid was further determined using a Waters Micromass ZQ equipped with a electrospray source. The electrospray source was switched to negative ion mode to acquire negative ion spectra. During the data acquisition, the mass spectrometer probe voltage was maintained at 2.5 kV; the cone voltage was maintained at 18 V and the extractor voltage 2 V; the source temperature was kept at 100° C. and the desolvation temperature 300° C.; and the drying gas flow rate was 200 L h$^{-1}$. The succinic acid was dissolved in MeOH—H$_2$O (90:9.5) and was injected into the carrier gas stream of the electrospray source at a flow rate of 5 µL min$^{-1}$ through a Hamilton 250 µL syringe by using a syringe pump. The mass spectrum of succinic acid showed a molecular ion at m/z: 118 and molecular formula C$_4$H$_6$O$_4$. $^1$HNMR and $^{13}$CNMR Spectra in CD$_3$OD were obtained on a Bruker DRX 500 NMR Spectrometer at 500 MHz and 125 MHz respectively. The structure of succinic acid and its chemical shifts assignment are as follows:

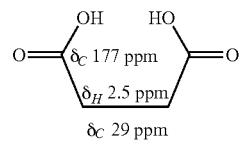

C. Antifouling (Antibacterial and Anti-Larval Settlement) Effects (1) 3-chloro-2,5-dihydroxy benzyl alcohol Antibacterial activity was tested against bacteria using an agar disc diffusion assay method. Sterile paper discs (6 mm i.d.) impregnated with the substance under test at a concentration of 50 µg disc$^{-1}$ were applied onto the surface of an agar plate (plastic Petri dish) inoculated with one strain with sterile forceps and gently pressed down to ensure good contact with the surface. Blank discs treated with the same volume of DMSO were added. A control disc, containing streptomycin was used. After the application of discs, the plates were incubated at 30° C. for 24 h, and then the size of the inhibition zone was measured.

Results are summarized in Table 7. As shown, 3-chloro-2, 5-dihydroxy benzyl alcohol was very active in inhibiting bacterial growth.

TABLE 7

ANTIMICROBIAL ACTIVITY OF 3-CHLORO-2,5-DIHYDROXY BENZYL ALCOHOL

| Bacteria | Inhibition Zone Width (mm) for Antibiotic Applied (50 μg/disc) | |
|---|---|---|
| | 3-Chloro-2,5-dihydroxy benzyl alcohol | Streptomycin |
| (a) Larvae settlement inducing bacteria | | |
| Micrococcus luteus | 6.0 | 6.5 |
| Vibrio sp. (NAP-4) | 4.0 | 4.0 |
| Pseudoalteromonas sp. | 5.5 | 6.0 |
| Vibrio fluvialis | 5.5 | 4.0 |
| Staphylococcus haemolyticus | 6.0 | 6.0 |
| Staphylococcus aureus | 5.5 | 3.5 |
| Ruegeria sp. | 3.5 | 4.5 |
| II. PATHOGEN BACTERIA | | |
| Shewanella algae | 4.5 | 7.0 |
| Moraxella phenylpyruvica | 5.5 | 0.0 |
| Pseudoalteromonas piscida | 5.0 | 5.0 |
| Vibrio harveyi | 3.5 | 3.0 |

Anti-larval settlement activity of 3-chloro-2,5-dihydroxy benzyl alcohol (compound 1) was conducted using 24-well polystyrene plates. Pure compound was dissolved in DMSO and added to autoclaved FSW at different concentrations. Competent *Balanus amphitrites* larvae (10±2 individuals) were added to each well with 1 ml testing solution in 5 replicates, and wells containing FSW (filtered seawater) served as control. The 24-well plates were incubated at 30° C. for 24 h. The percent settlement was determined by counting the number of settled larvae under a dissecting microscope. In all bioassays, FSW served as the control. Statistical calculations were performed with the SPSS (Statistical Package for the Social Sciences) software package, Version 11.

Figure 4:
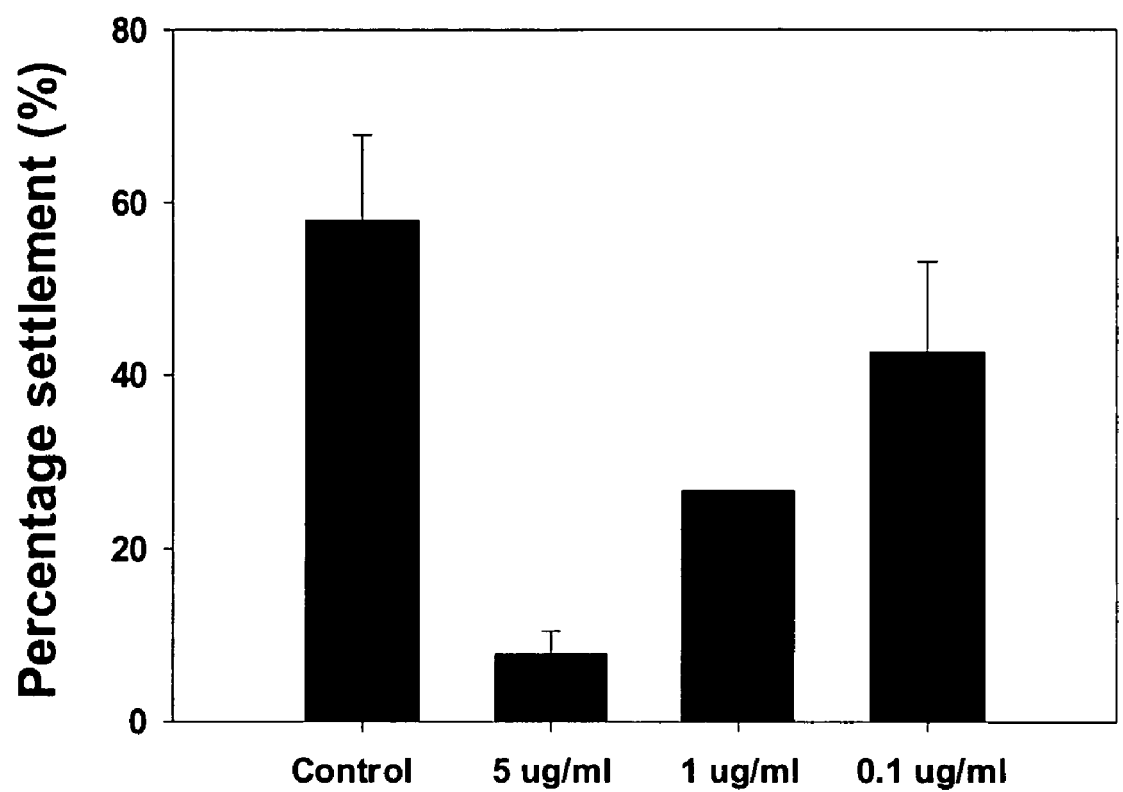
FIG. 4 shows the effect of 3-chloro-2,5-dihydroxybenzyl alcohol on barnacle larval settlement.

Referring to FIG. 4, 3-chloro-2,5-dihydroxy benzyl alcohol effectively inhibited barnacle larval settlement at the concentration of 5 μg ml$^{-1}$, with about 10% settlement in contrast to 60% in the control. The compound started showing anti-settlement effects at a contraction as low as 0.1 μg ml$^{-1}$.

The larval bioassay was conducted according to Rittschof et al. (1994), which is incorporated by reference herein in its entirety. The $EC_{50}$ was 3.5 μg ml$^{-1}$ and the $LC_{50}$ is 266.7 μg ml$^{-1}$. The therapeutic ratio $LC_{50}/EC_{50}$ of the Compound 1 was 76.2, meaning that this compound was not toxic. Toxic compounds, such as heavy metals, have a therapeutic ratio close to 1 (Rittschof et al. 1992) while nontoxic antifouling compounds have ratios from approximately 10 to over 100,000 (Avelin et al. 1993).

(2) Cyclo (D)-Pro-(D)-Phe and 3-methyl-N-(2-phenylethyl) butanamide

Antibacterial activity was tested against bacteria using agar disc diffusion assay. Sterile paper discs (6 mm i.d.) impregnated with the substance under test at a concentration of 50 μg disc$^{-1}$ were applied onto the surface of an agar plate (plastic Petri dish) inoculated with one strain with sterile forceps and gently pressed down to ensure good contact with the surface. Blank discs treated with the same volume of DMSO were added. A control disc containing streptomycin was used. After the application of discs, the plates were incubated at 30° C. for 24 h. The size of the inhibition zone was measured. The results are presented in Table 8 and Table 9 for Cyclo (D)-Pro-(D)-Phe and b3-methyl-N-(2-phenylethyl)butanamide, respectively.

TABLE 8

ANTIMICROBIAL OF CYCLO (D)-PRO-(D)-PHE

| Testing Bacteria | Inhibition Zone Width (mm) | |
|---|---|---|
| | Streptomycin (100 μg) | Cyclo-(Pro-Phe) (50 μg/disc) |
| Larvae settlement inducing bacteria | | |
| Micrococcus luteus | 6.7 ± 0.6 | 0.5 ± 0.0 |
| Vibrio sp. (NAP-4) | 5.7 ± 0.6 | 1.3 ± 0.6 |
| Pseudoalteromonas sp. | 4.0 ± 1.0 | 1.7 ± 0.6 |
| Vibrio fluvialis | 3.0 ± 0.0 | 1.2 ± 0.7 |
| Staphylococcus haemolyticus | 3.0 ± 0.0 | 0.8 ± 0.3 |
| Rhodovulum sp. | 5.3 ± 1.2 | 0.0 ± 0.0 |
| Vibrio halioticoli | 4.3 ± 0.6 | 0.0 ± 0.0 |
| Vibrio alginolyticus | 6.7 ± 2.3 | 0.0 ± 0.0 |
| Pathogen bacteria | | |
| Loktanella hongkongensis | 4.0 ± 0.0 | 1.3 ± 0.6 |
| Vibrio furnissii | 2.3 ± 0.6 | 0.0 ± 0 |
| Vibrio vulnificus | 3.3 ± 0.8 | 1.0 ± 0.1 |
| Shewanella algae | 6.3 ± 1.2 | 0.0 ± 0 |
| Vibrio. harveyi | 6.0 ± 0.0 | 0.5 ± 0 |
| Pseudoalteromonas piscida | 3.0 ± 1.0 | 0.0 ± 0 |
| Moraxella phenylpyruvica | 9.0 ± 0.0 | 0.0 ± 0 |

TABLE 9

ANTIMICROBIAL OF 3-METHYL-N-(2-PHENYLETHYL)BUTANAMIDE (Compound 3)

| Testing Bacteria | Inhibition Zone Width (mm) | |
|---|---|---|
| | Streptomycin (100 μg) | 3-methyl-N-(2-phenylethyl) butanamide (50 μg/disc) |
| Larvae settlement inducing bacteria | | |
| Micrococcus luteus | 6.7 ± 0.6 | 3.3 ± 0.6 |
| Vibrio sp. (NAP-4) | 5.7 ± 0.6 | 0.0 ± 0.0 |
| Pseudoalteromonas sp. | 4.0 ± 1.0 | 0.0 ± 0.0 |
| Vibrio fluvialis | 3.0 ± 0.0 | 0.0 ± 0.0 |
| Staphylococcus haemolyticus | 3.0 ± 0.0 | 0.5 ± 0.0 |
| Rhodovulum sp. | 5.3 ± 1.2 | 3.0 ± 0.5 |
| Vibrio halioticoli | 4.3 ± 0.6 | 0.0 ± 0.0 |
| Vibrio alginolyticus | 6.7 ± 2.3 | 1.7 ± 0.6 |
| Pathogen bacteria | | |
| Loktanella hongkongensis | 4.0 ± 0.0 | 0.5 ± 0.0 |
| Vibrio furnissii | 2.3 ± 0.6 | 0.0 ± 0.0 |
| Vibrio vulnificus | 3.3 ± 0.8 | 1.2 ± 0.7 |
| Shewanella algae | 6.3 ± 1.2 | 1.3 ± 0.6 |
| Vibrio harveyi | 6.0 ± 0.0 | 0.0 ± 0.0 |
| Pseudoalteromonas piscida | 3.0 ± 1.0 | 1.5 ± 0.0 |
| Moraxella phenylpyruvica | 9.0 ± 0.0 | 0.0 ± 0.0 |

Toxicity of cyclo (D)-Pro-(D)-Phe was determined using 24-well polystyrene plates. Pure compound was dissolved in DMSO and added to autoclaved FSW to form different concentrations. Competent *Balanus amphitrites* larvae (10±2 individuals) were added to each well with 1 ml testing solution in 5 replicates. The wells containing FSW served as the control. The 24-well plates were incubated at 30° C. for 24 h. The percent mortality was determined by counting the number of dead larvae under a dissecting microscope. Both Cyclo (D)-Pro-(D)-Phe and butanamide did not induce any toxic symptoms at the concentration of 50 μg ml$^{-1}$.

Figure 5:
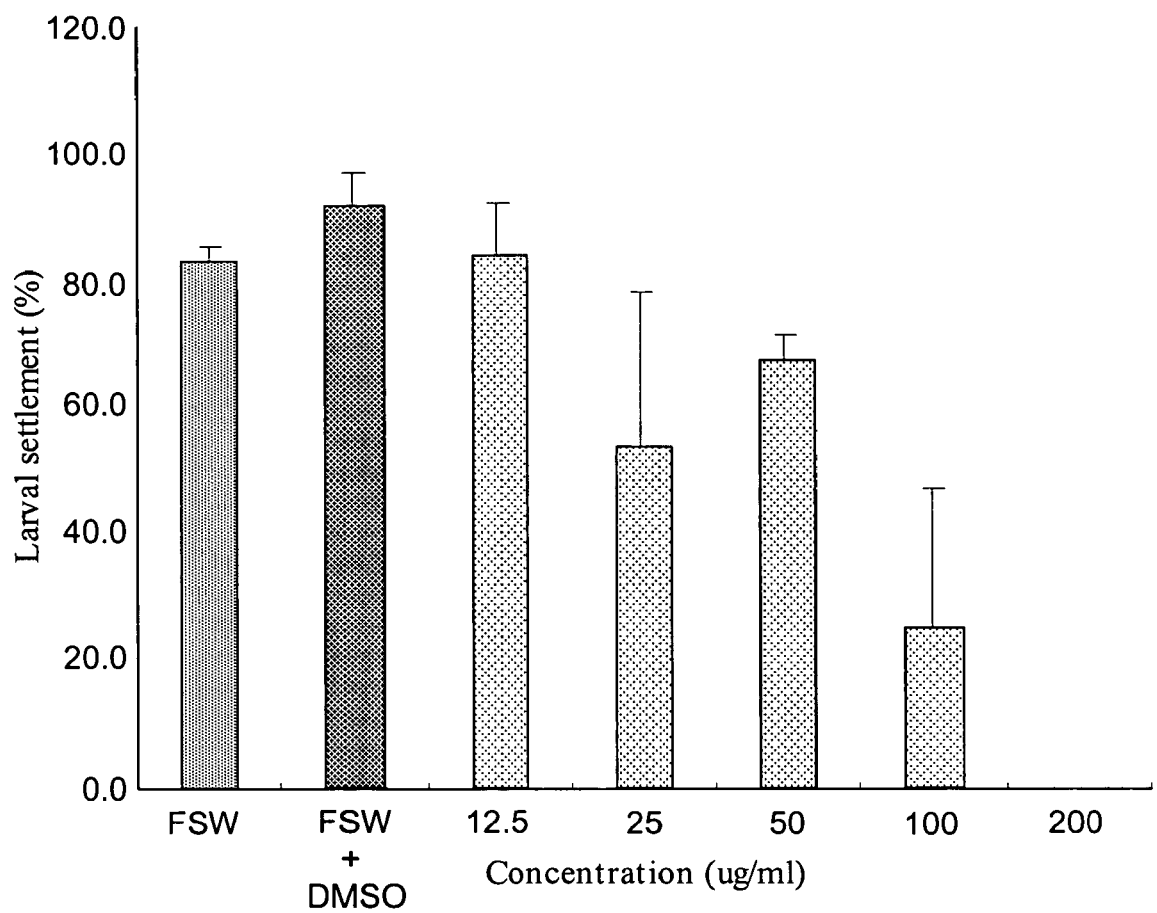
FIG. 5 shows the anti-larval settlement activity of cyclo-(Phe-Pro) against barnacle *Balanus amphitrite*.
Figure 6:
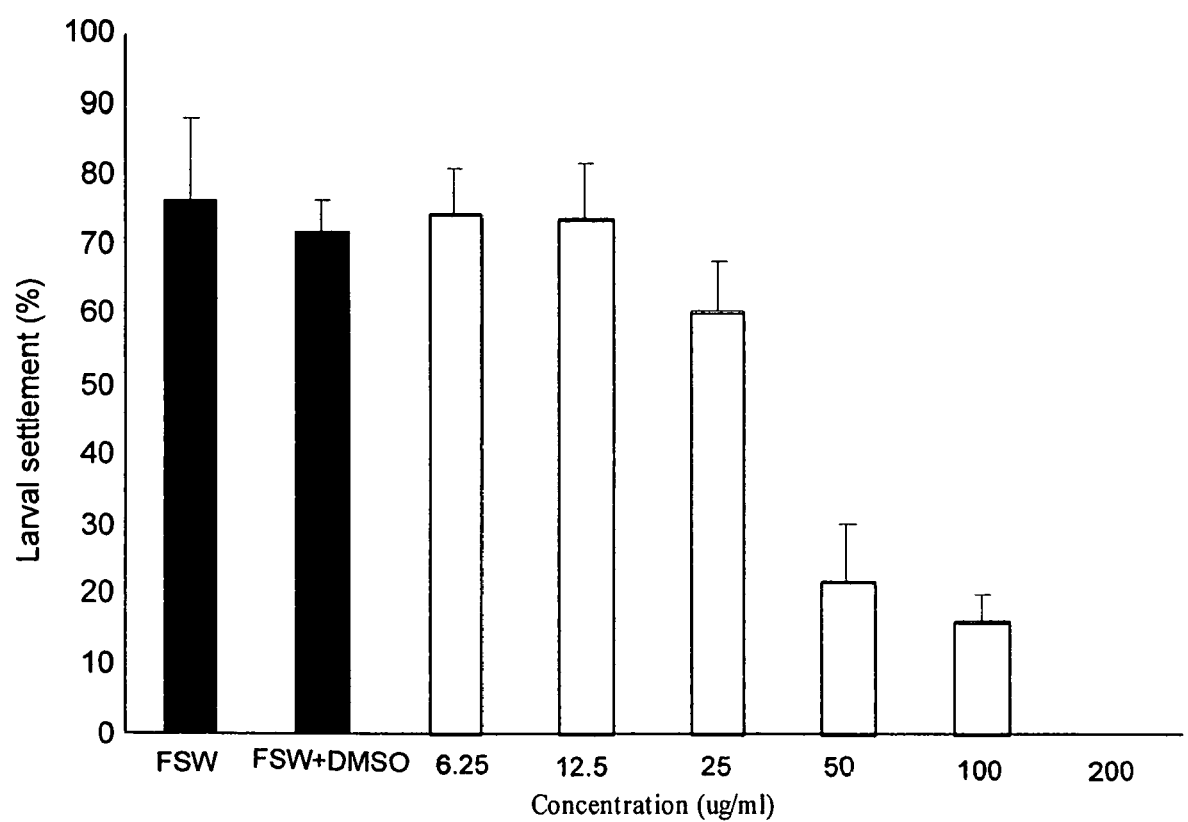
FIG. 6 shows the anti-larval settlement activity of 3-methyl-N-(2-phenylethyl) butanamide against barnacle *Balanus amphitrite*.

FIG. 5 and FIG. 6 show the anti-larval settlement activity of cyclo-(Phe-Pro) (Compound 2) and 3-methyl-N-(2-phenylethyl)butanamide (Compound 3), respectively, against the barnacle *Balanus amphitrite* larvae. The assay was conducted according to Rittschof et al. (1994). Data plotted are means+ SD of five replicates. For cyclo-(Phe-Pro), the EC50 was 67.3 µg ml$^{-1}$ and the LC50 was 114.8 µg ml$^{-1}$, giving a therapeutic ratio LC50/EC50 of 1.70. For 3-methyl-N-(2-phenylethyl) butanamide, the EC50 was 36.5 µg ml$^{-1}$ and the LC50 was 81.4 µg ml$^{-1}$. The therapeutic ratio LC50/EC50 of 3-methyl-N-(2-phenylethyl) butanamide was 2.23. The results suggest that both compounds are low toxic according to the above mentioned standards (Rittschof et al. 1992 and Avelin et al. 1993, each of which is incorporated by reference herein in its entirety).

(3) Succinic Acid

Antibacterial activity of the succinic acid was tested using disc diffusion assay method. The target bacteria included nine bacterial strains that can induce the larval settlement of *H. elegans*: *Vibrio halioticoli*, *Micrococcus luteus*, *Pseudoalteromonas* sp., *Loktanella hongkongensis*, *Rhodovulum* sp. (MB253), *Vibrio fluvialis*, *Staphylococcus haemolyticus*, *Ruegeria* CtaxMed-2, *Vibrio* sp. (NAP-4) and 5 strains of marine pathogenic bacteria: *Vibrio furnissii*, *Vibrio vulnificus*, *Shewanella algae*, *Staphylococcus aureus*, and *Moraxella phenylpyruvica*. Specifically, sterile paper discs (6 mm i.d.) impregnated with the substance under test at a concentration of 100 µg disc$^{-1}$ were applied onto the surface of an agar plate (plastic Petri dish) inoculated with one strain with sterile forceps. Blank discs treated with the same volume of acetonitrile were added. The disc containing streptomycin at a concentration of 10 µg disc$^{-1}$ was used as control. After application of discs, the plates were incubated at 30° C. for 24 h and then the inhibition zone was measured.

For determining anti-larval settlement activity, adult *Balanus amphitrile* (Darwin) were collected from the intertidal zone in Hong Kong (22°19'N, 114°16'E). Nauplii obtained from several adults were mass-reared to cyprid stage at a density of 2 larvae ml$^{-1}$ in 0.22-µm-filtered seawater with 30 ppt salinity (FSW) using *Chaetoceros gracilis* Schutt as food and a rearing temperature of 28° C. Newly transformed cyprids were used for the experiment.

Anti-larval settlement activity of succinic acid against *B. amphitrite* was determined using 24-well polystyrene plates. Pure compound was dissolved in autoclaved FSW ranged from 60-140 µg ml$^{-1}$ for *B. amphitrite*. Competent larvae (15±2 individuals) were added to each well with 1 ml testing solution in 5 replicates, and wells containing FSW served as the control. The 24-well plates were incubated at 30° C. for 24 h. The percent larval settlement was determined by counting the number of settled individuals under a dissecting microscope and expressed as a proportion of the total number of larvae in the well.

Figure 7:
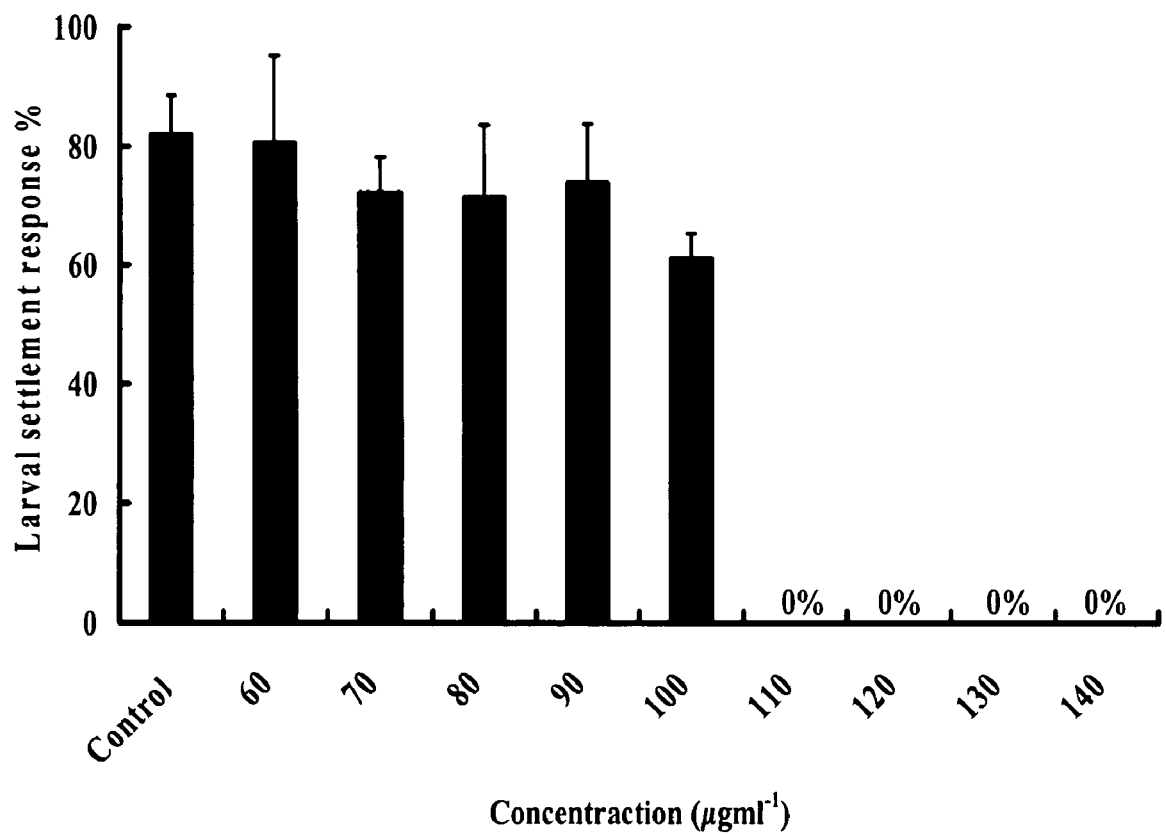
FIG. 7 shows the anti-larval settlement activity of succinic acid against barnacle *Balanus amphitrite*.
Figure 8:
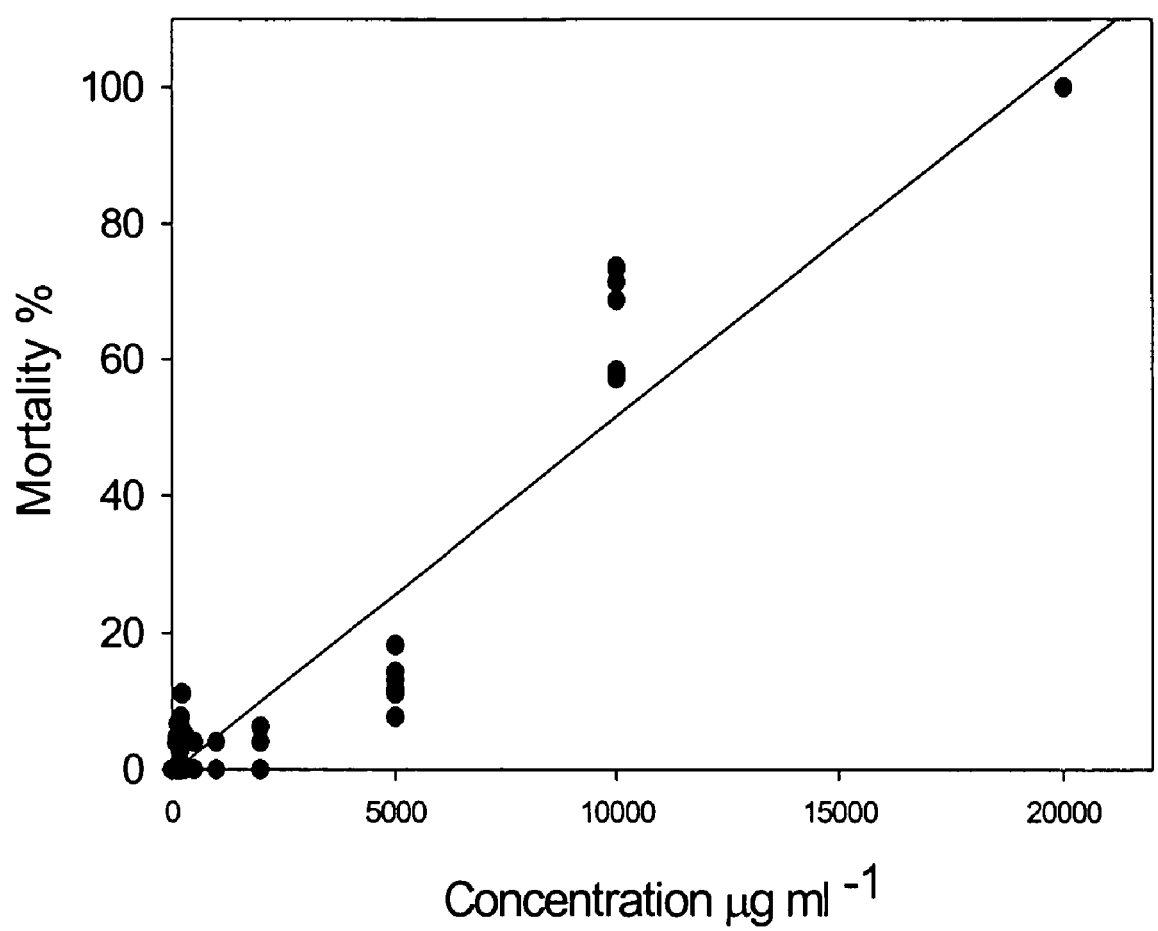
FIG. 8 shows the effect of succinic acid on larval mortality of *Balanus amphitrite*.

Referring to FIG. 7, succinic acid showed anti-larval settlement effects on barnacle *B. amphitrite* at concentration 110 µg ml$^{-1}$. One-way ANOVA analysis showed that succinic acid significantly reduced the percentage of larval settlement of *B. amphitrite* ($F_{9,40}$=133.9, p<0.001). Succinic acid also increased the mortality rate of *B. amphitrite* when the concentration higher than 110 µg ml$^{-1}$. One-way ANOVA analysis showed that succinic acid significantly increased the mortality rate of *B. amphitrite* ($F_{9,40}$=321.1, p<0.001). The therapeutic ratio $LC_{50}/EC_{50}$ was 94.1, indicating this compound as nontoxic. FIG. 8 shows the effect of succinic acid on the percentage of larval mortality of *B. amphitrite*.

Immobilization of succinic acid into gel matrix followed a protocol of Harder et al. (2004). Specifically, a 4% (W/V) of Phytagel solution was prepared by dissolving Phytagel® (Sigma Chemical) in distilled water at 90° C. After cooling to 70° C., a concentrated solution of succinic acid (5.5 mg ml$^{-1}$) was vigorously mixed with the Phytagel® solution in 15-ml centrifuge tubes to yield a final concentration of 550 µg ml$^{-1}$ succinic acid. The tubes were closed and immersed upside down in a 60° C. water bath to allow the Phytagel® to slowly solidify to transparent cylinders. The Phytagel® cylinders were removed and sliced into 1-cm-thick gel discs using a sterile razor blade. Control Phytagel® discs were prepared accordingly with doubled-distilled water. There were 48 discs for the treatments and the controls of the three-day of experiment: 18 discs were used for the determination of the release rate of succinic acid from the Phytagel®—9 discs were fixed on consecutive days in 4% of formaldehyde in seawater for bacterial counts (FIG. 9); 12 discs were used consecutive days for running the larval settlement bioassays (FIG. 10).

Figure 9:
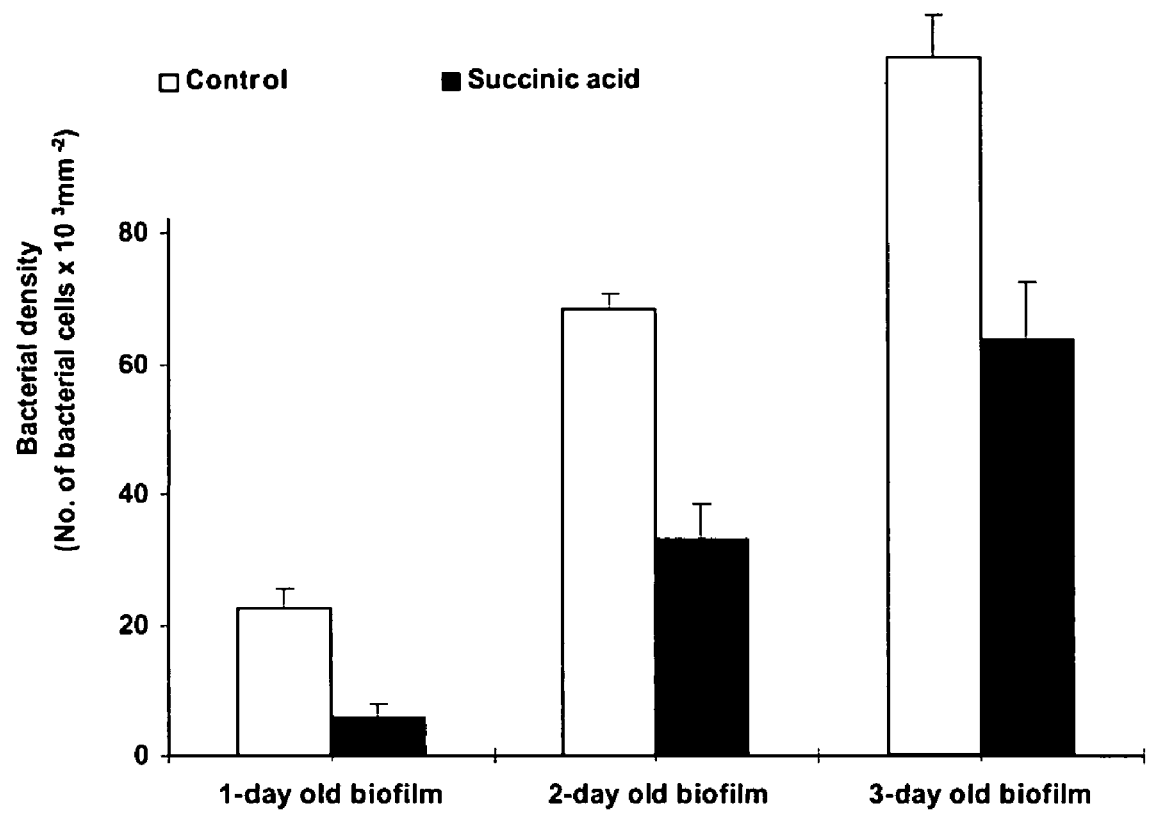
FIG. 9 shows bacterial cell densities of 1-, 2- and 3-day-old biofilm formed on the Phytagel surfaces with double-distilled water (control) and with succinic acid.
Figure 10:
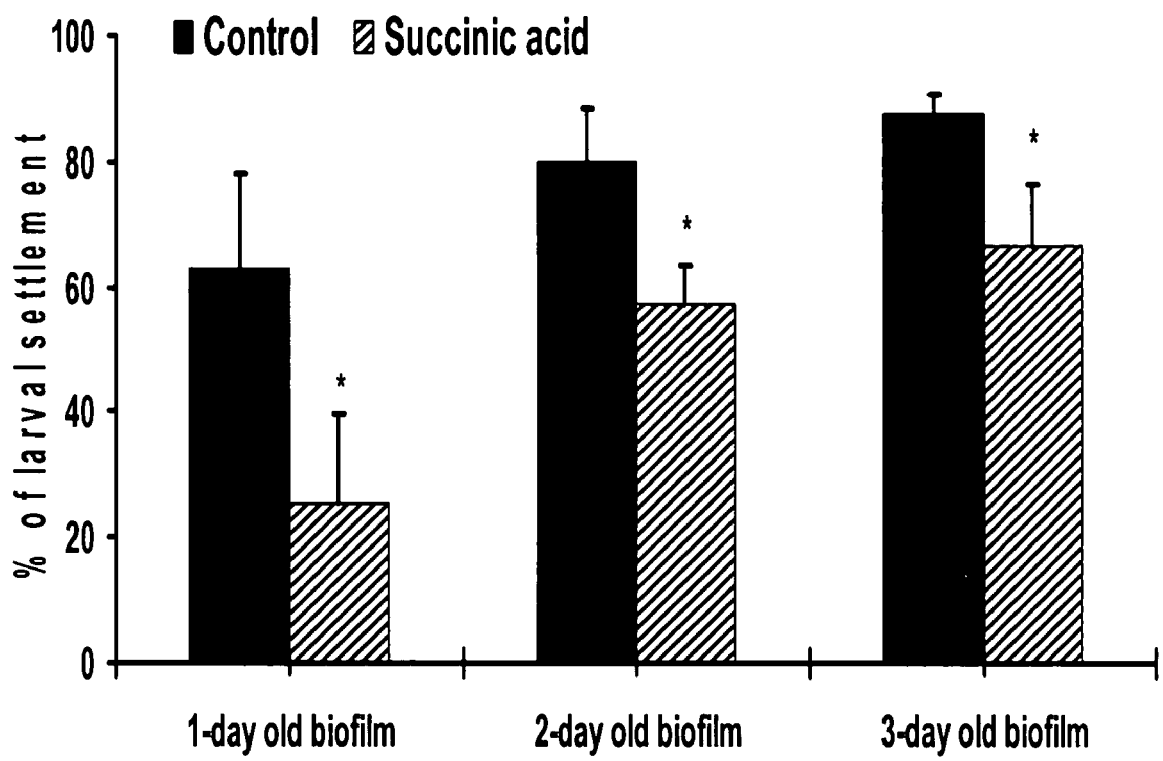
FIG. 10 shows larval settlement in response to 1-, 2- and 3-day-old biofilm formed on the Phytagel surfaces with succinic acid and without it (control).
Figure 11:
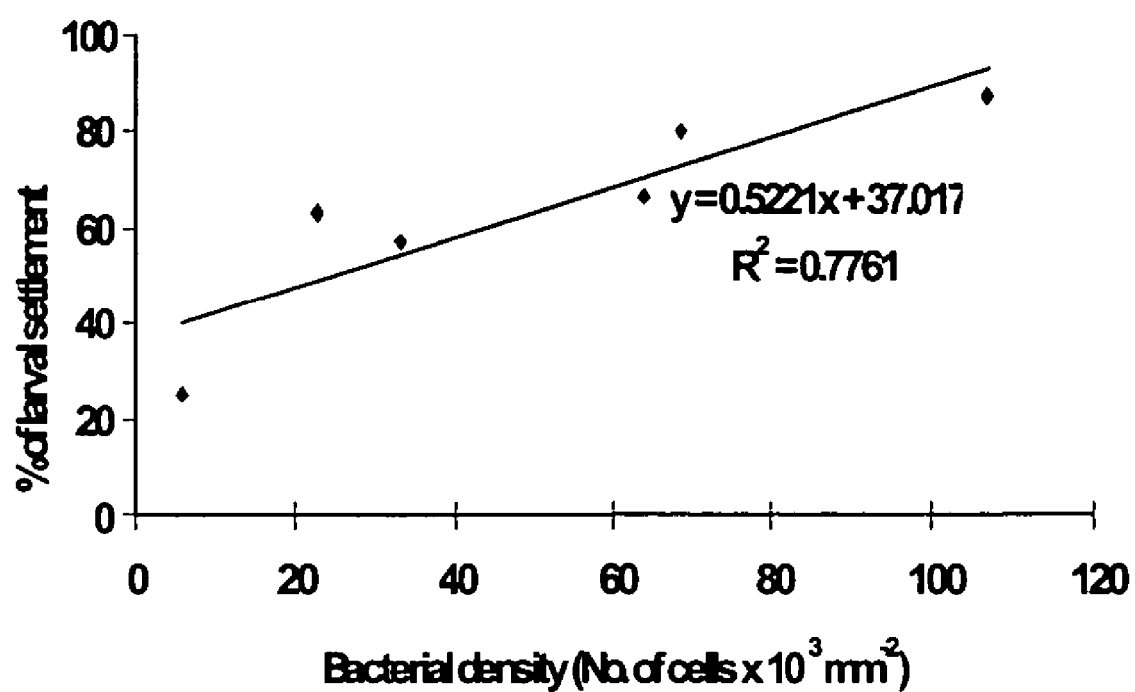
FIG. 11 is a line chart showing the correlation between the bacterial cell densities on the Phytagel surfaces with succinic acid and the percentage of larval settlement of *Hydroides elegans*.
Figure 12:
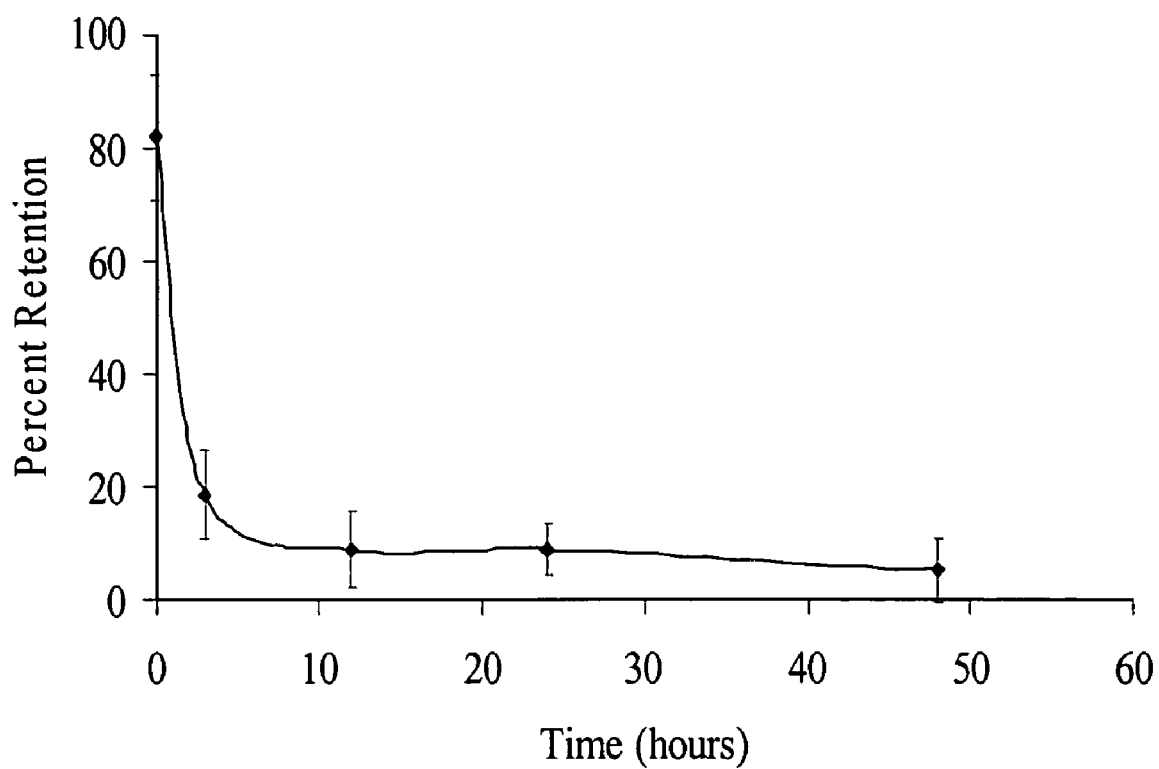
FIG. 12 shows the percentage of retention of succinic acid in Phytagel matrix over time.

FIG. 9 shows bacterial cell densities of 1-, 2- and 3-day-old biofilm formed on the Phytagel surfaces with double-distillated water (controls) and with succinic acid (concentration=550 µg ml$^{-1}$). Data are means±SD of 3 replicates. FIG. 10 shows the larval settlement in response to 1-, 2- and 3-day-old biofilm formed on the Phytagel surface with succinic acid (concentration=550 µg ml$^{-1}$) and without it (control). Data are expressed as mean±SD for 4 replicates. FIG. 11 is a line chart, showing the correlation between bacterial cell densities on the phytagel surfaces with succinic acid and without it (control) and the percentage of larval settlement of *H. elegans*. FIG. 12 shows the retention percentage of succinic acid in Phytagel matrix when immersed in fresh seawater. To determine the anti-larval effect of succinic acid after being incorporated into non-toxic paint matrix, the following procedure was followed. Succinic acid was mixed with non-toxic paint (Levis®Ferro Vernis) at concentration of 10% (10 mg/100 ml) and 1% (1 mg/100 ml). Non-toxic paint (positive control) and antifouling paint (International® Interspeed Ultra biocidal paint) were used as controls. Five replicated plastic panels (size 100 cm$^2$) of each treatment were painted. Panels were exposed to macrofouling for 7 days. The number of settled *Hydroides elegans* were counted and transformed to individual per m$^2$. The release rate of succinic acid was determined under the static conditions in the laboratory.

Figure 13:
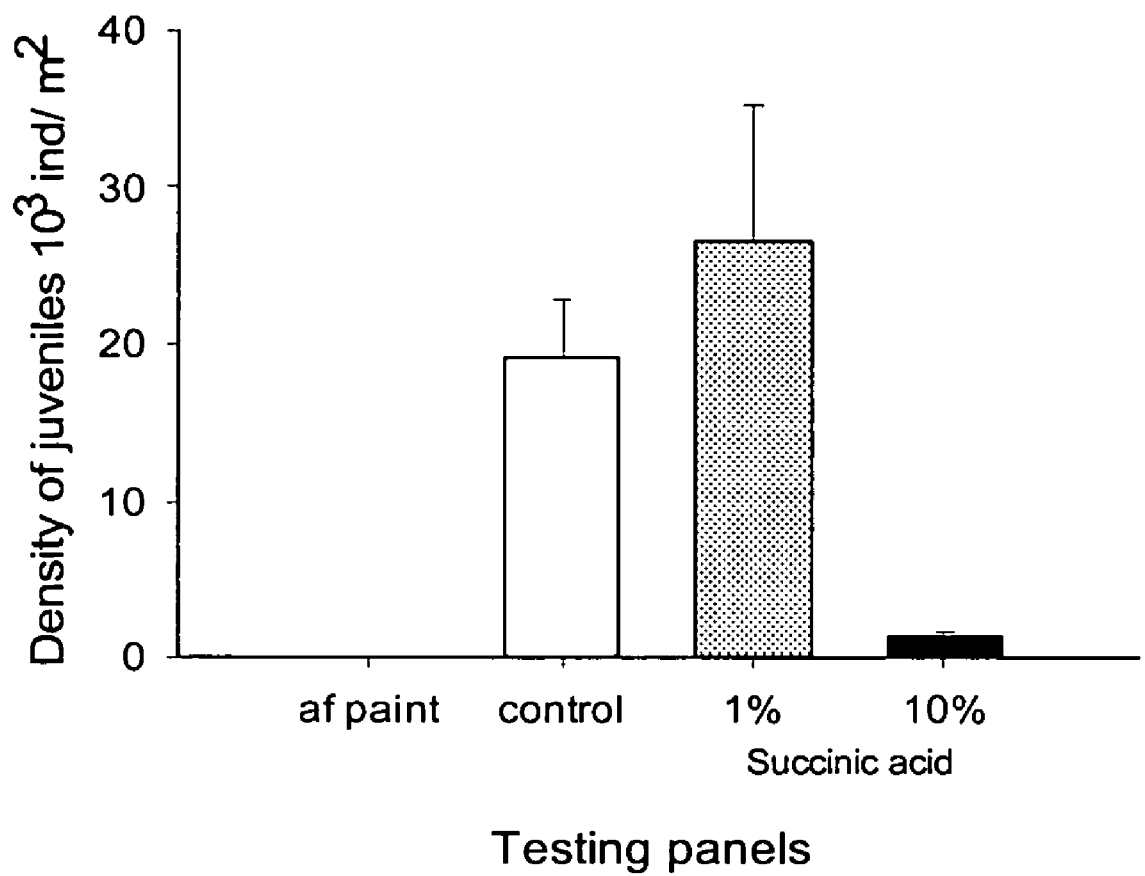
FIG. 13 shows the density of juveniles *Hydroides elegans* on experimental coatings with 1% and 10% of succinic acid.
Figure 14:
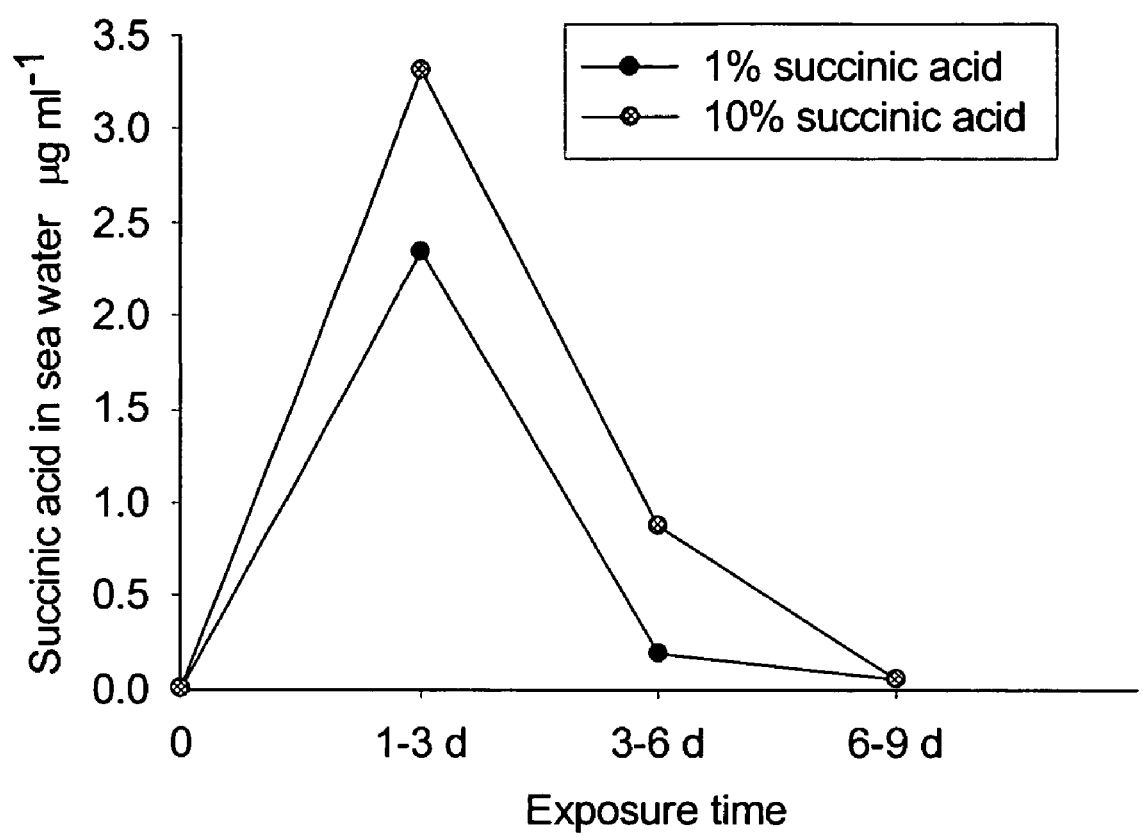
FIG. 14 shows the concentration of succinic acid released from non-toxic paint in the static laboratory experiments, indicating that most of succinic acid released during first 3-6 days of experiments.

FIG. 13 shows the density of juveniles *Hydorides elegans* on experimental coatings with 1% (1 mg/100 ml) and 10% (10 mg/100 ml) of succinic acid. Antifouling paint (af paint) and non-toxic paint (control) were used as positive and negative controls. FIG. 14 shows the concentration of succinic acid released from non-toxic paint in the static laboratory experiments, indicating that most of succinic acid released from first 3-6 days of experiments.

D. Making Functional Derivatives

Although the present invention provides four specific antibacterial and antifouling compounds with a common feature that they all naturally occur in marine microorganisms and are non-toxic to human and animals, it may serve as a new paradigm in search for antifouling (antibacterial and anti-larval settlement) agents that are environment-friendly: using naturally occurring compounds with desirable effects as the "lead compound" for further man-made modifications. These modifications may result in better effects or lower production cost or other advantages (such as better bio-availabilities).

It is further contemplated, as a person with ordinary skill in the art would understand, that the above compounds may be made in various possible racemic, enantiomeric or diastereoisomeric isomer forms, may form salts with mineral and organic acids, and may also form derivatives such as N-oxides, prodrugs, bioisosteres. "Prodrug" means an inactive form of the compound due to the attachment of one or more specialized protective groups used in a transient manner to alter or to eliminate undesirable properties in the parent molecule, which is metabolized or converted into the active compound inside the body (in vivo) once administered. "Bioisostere" means a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Making suitable prodrugs, bioisosteres, N-oxides, pharmaceutically acceptable salts or various isomers from a known compound (such as those disclosed in this specification) are within the ordinary skill of the art. Therefore, the present invention contemplates all suitable isomer forms, salts and derivatives of the above disclosed compounds.

In the context of the present invention, the term "functional derivative" means a prodrug, bioisostere, N-oxide, pharmaceutically acceptable salt or various isomer from the above-disclosed specific compound, which may be advantageous in one or more aspects compared with the parent compounds. Making functional derivatives may be laborious, but the technologies involved are well known in the art. Various high-throughput chemical synthetic methods are available. For example, combinatorial chemistry has resulted in the rapid expansion of compound libraries to be coupled with various highly efficient bio-screening technologies.

E. Making Antifouling Coatings

Once a desirable antifouling compound is identified, it is within the ordinary skill of the art to formulate and produce antifouling coatings by incorporating the active ingredient. For example, the active compound may be dissolved or dispersed in a mixture of natural resins and a vinyl chloride vinyl acetate copolymer, known as the film-forming components. Other polymers, which are hydrolysable, soluble or insoluble resins, may be used as the film-forming components. Once applied, the coating should provide an effective amount of the active ingredient on the submarine surface to protect it from fouling.

In the context of the present invention, the amount of active antifouling (antibacterial or anti-larval settlement) ingredient used in a formulation should be sufficient to effect a beneficial therapeutic or antifouling response under a particular circumstance, and is referred to by the term "effective amount" which can be determined by one of ordinary skill in the art.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of preventing biofouling on a submarine surface, comprising a step of applying a coating on said submarine surface, said coating comprising a compound selected from the group consisting of 3-chloro-2,5-dihydroxy benzyl alcohol, cyclo-(Pro-Phe), and 3-methyl-N-(2-phenylethyl)butanamide; said method being applicable to microfouling, macrofouling, or both microfouling and macrofouling.

2. The method of claim 1, wherein said coating comprises 3-chloro-2,5-dihydroxy benzyl alcohol.

3. The method of claim 1, wherein said coating comprises cyclo-(Pro-Phe).

4. The method of claim 1, wherein said coating comprises 3 methyl-N-(2-phenylethyl)butanamide.

5. An antifouling coating, comprising a film-forming component and a compound selected from the group of consisting 3-chloro-2,5-dihydroxy benzyl alcohol, cyclo-(Pro-Phe), and 3-methyl-N-(2-phenylethyl)butanamide; said coating possessing an antifouling activity where applied to a submarine surface as compared to an uncoated control submarine surface.

6. The antifouling coating of claim 5, wherein said film-forming component comprising one or more polymers selected from hydrolysable, soluble, or insoluble resins.

7. The antifouling coating of claim 6, wherein said compound is 3-chloro-2,5-dihydroxy benzyl alcohol.

8. The antifouling coating of claim 6, wherein said compound is cyclo-(Pro-Phe).

9. The antifouling coating of claim 6, wherein said compound is 3-methyl-N-(2-phenylethyl)butanamide.

* * * * *

SEQUENCE LISTING

```
<160> NUMBER OF SEQ ID NOS: 5

<210> SEQ ID NO 1
<211> LENGTH: 514
<212> TYPE: DNA
<213> ORGANISM: Ampelomyces sp
<220> FEATURE:
<221> NAME/KEY: misc_feature
<222> LOCATION: 26
<223> OTHER INFORMATION: n = A,T,C or G

<400> SEQUENCE: 1
gtactgcgga aggatcatca ctagangtag taggctttgc ctgctatctc ttacccatgt      60
ttttgagtac cttacgtttc ctcggtgggt ccgcccaccg attggacaaa tttaaaccct     120
ttgcagttga aatcagcgtc tgaaaaaact taatagttac aactttcaac aacggatctc     180
ttggttctgg catcgatgaa gaacgcagcg aaatgcgata agtagtgtga attgcagaat     240
tcagtgaatc atcgaatctt tgaacgcaca ttgcgcccct tggtattcca tggggcatgc     300
ctgttcgagc gtcatttgta ccttcaagct ctgcttggtg ttgggtgttt gtctcctgta     360
gactcgcctt aaaacaattg gcagccggcg tattgatttc ggagcgcagt acatctcgcg     420
ctttgcactc ataacgacga catccaaaag tacattttta cactcttgac ctcggatcag     480
gtagggatac ccgctgaact ttagcatatc aata                                  514

<210> SEQ ID NO 2
<211> LENGTH: 661
<212> TYPE: DNA
<213> ORGANISM: Fusarium sp.
<220> FEATURE:
<221> NAME/KEY: misc_feature
<222> LOCATION: 17
<223> OTHER INFORMATION: n = A,T,C or G
```

-continued

```
<400> SEQUENCE: 2
ttggggctgt acaaagnctg agtatgatta tagggacagt cgggggcatc agtattcaat      60
tgtcagaggt gaaattcttg gatttattga agactaacta ctgcgaaagc atttgccaag     120
gatgttttca ttaatcagga acgaaagtta ggggatcgaa gacgatcaga taccgtcgta     180
gtcttaacca taaactatgc cgactaggga tcggacggtg ttattttttg acccgttcgg     240
caccttacga gaaatcaaag tgcttgggct ccaggggag tatggtcgca aggctgaaac      300
ttaaagaaat tgacggaagg gcaccaccag gggtggagcc tgcggcttaa tttgactcaa     360
cacggggaaa ctcaccaggt ccagacacaa tgaggattga cagattgaga gctctttctt     420
gatttgtggg tggtggtgca tggccgttct tagttggtgg agtgatttgt ctgcttaatt     480
gcgataacga acgagacctt aacctgctaa atagcccgta ttgctttggc agtaacgctg     540
gcttcttcag agggactatc ggctcagccg atggcaagtt tgagggcaat aaaccagggt     600
cctgtgatgc ccttagatgt tcctggggcc ggacgcagcg ctacactggc cggaagcccg     660
t                                                                    661

<210> SEQ ID NO 3
<211> LENGTH: 532
<212> TYPE: DNA
<213> ORGANISM: Fusarium sp.
<220> FEATURE:
<221> NAME/KEY: misc_feature
<222> LOCATION: 5
<223> OTHER INFORMATION: n = A,T,C or G

<400> SEQUENCE: 3
aatantcagc agagggaggg atcattacga gtttacaact cccaaacccc tgtgaacata      60
cctatacgtt gcctcggcgg atcagcccgc gtccccgtaa aacgggacgg cccgcccgag     120 cgaccccctaa actctgtttt ctagtggaac ttctgagtaa aacaaacaaa taaatcaaaa     180
ctttcaacaa cggatctctt ggttctggca tcgatgaaga acgcagcaaa atgcgataag     240
taatgtgaat tgcagaattc agtgaatcat cgaatctttg aacgcacatt gcgcccgcca     300
gtattctggc gggcatgcct gttcgagcgt catttcaacc ctcaagctca gcttggtgtt     360
gggactcgcg gtaacccgcg ttccccaaat cgattggcgg tcacgtcgag cttccatagc     420
gtagtaatca tacacctcgt tactggtaat cgtcgcggca cgccgttaaa ccccaacttc     480
tgaatgttga cctcggatca ggtaggaata cccgtgaatt aagcatatca ta            532

<210> SEQ ID NO 4
<211> LENGTH: 734
<212> TYPE: DNA
<213> ORGANISM: Marine fungus UST03110-009
<220> FEATURE:
<221> NAME/KEY: misc_feature
<222> LOCATION: 3, 4
<223> OTHER INFORMATION: n = A,T,C or G

<400> SEQUENCE: 4
cgnnggctgt atttatgtgg tttcgtatga ctgcgtaatg attaataggg acagtcgggg      60
gcatcagtat tcaattgtca gaggtgaaat tcttggattt attgaagact aactactgcg     120
aaagcatttg ccaaggatgt tttcattaat cagtgaacga agttagggg atcgaagacg      180 atcagatacc gtcgtagtct taaccataaa ctatgccgac tagggatcgg cggtgtttc     240 tattgtgacc cgctcggcac cttacgagaa atcaaagtgt ttgggttctg ggggagtat      300 ggtcgcaagg ctgaaactta agaaattga cggaagggca ccaccaggcg tggagcctgc      360
```

```
ggcttaattt gactcaacac ggggaaactc accaggtcca gatgaaataa ggattgacag      420
attgagagct ctttcttgat ttttcaggtg gtggtgcatg gccgttctta gttcgtgggg      480
tgacttgtct gcttaattgc gataacgaac gagaccttaa cctgctaaat agccaggcta      540
gctttggctg gtcgccggct tcttagaggg actatcggct caagccgatg gaagtttcga      600
ggcaataaca ggtctgtgat gcccttagat gttctgggcc gacgcgcgct acactgacag      660
agccaacgag ttcttttccc ttggccggaa ggtctgggta atcttgttaa aactctgtcg      720
tgctggggat agac                                                        734

<210> SEQ ID NO 5
<211> LENGTH: 651
<212> TYPE: DNA
<213> ORGANISM: Marine fungus UST03110-009
<220> FEATURE:
<221> NAME/KEY: misc_feature
<222> LOCATION: 32, 33, 49
<223> OTHER INFORMATION: n = A,T,C or G

<400> SEQUENCE: 5
tccgtataga tgcagctaga cggagggatc anngacattg ttcagcaanc aagcgatggc       60
gtcgtcctta gaaccgtctc cgtgcggctc ggggcggcgt ttcatcagcg ggcacgtcgc      120
ggcttcctgt tttcaggaag taatcccatc tagaatggac tcacgcgggg tcgtctgaat      180
ccttaacttt acgagaactc cccatactcc ttcggtgggg tgacctgccg ttggaaccaa      240
caaaaacctt ttttttgcat ctagcattac ctgttctgat acaaacaatc gttacaactt      300
tcaacaatgg atctcttggc tctggcactc gatgaagaac gcagcgaaat gcgataagta      360
gtgtgaattg cagaattcag tgaatcatcg aatctttgaa cgcacattgc gccccttggt      420
attccatggg gcatgcctgt tcgagcgtca tctacaccct caagctctgc ttggtgttgg      480
gcgtctgtcc cgcctccgcg cgtggactcg cccaaattc attggcagcg gtcttcttgc       540 cccctctcg cgcagcacat tgcgttctcg aggggtggcg gggcccggtc cacgaagcca      600
acattcaccc gttctttgac ctcggatcag gtagggatac cgtgattagc g              651
```